(12) United States Patent
Jo et al.

(10) Patent No.: US 11,970,445 B2
(45) Date of Patent: Apr. 30, 2024

(54) METHOD AND APPARATUS FOR RECOVERING AMIDE-BASED COMPOUND

(71) Applicant: LG CHEM, LTD., Seoul (KR)

(72) Inventors: Sanghwan Jo, Daejeon (KR); Joong Jin Han, Daejeon (KR); Hansol Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 755 days.

(21) Appl. No.: 17/054,729

(22) PCT Filed: Sep. 27, 2019

(86) PCT No.: PCT/KR2019/012634
§ 371 (c)(1),
(2) Date: Nov. 11, 2020

(87) PCT Pub. No.: WO2020/067797
PCT Pub. Date: Apr. 2, 2020

(65) Prior Publication Data
US 2021/0238137 A1    Aug. 5, 2021

(30) Foreign Application Priority Data

Sep. 28, 2018  (KR) .................. 10-2018-0116449
Sep. 26, 2019  (KR) .................. 10-2019-0119141

(51) Int. Cl.
| | | |
|---|---|---|
| *C07D 207/267* | (2006.01) | |
| *B01D 3/14* | (2006.01) | |
| *B01D 3/40* | (2006.01) | |
| *C08G 75/0259* | (2016.01) | |
| *C08G 75/0281* | (2016.01) | |

(52) U.S. Cl.
CPC ......... *C07D 207/267* (2013.01); *B01D 3/141* (2013.01); *B01D 3/40* (2013.01); *C08G 75/0259* (2013.01); *C08G 75/0281* (2013.01)

(58) Field of Classification Search
CPC ...... C07D 207/267; B01D 3/141; B01D 3/40; C08G 75/14; C08G 75/0209; C08G 75/0254; C08G 75/0263; C08G 75/0268; C08G 75/0259; C08G 75/025; C08G 75/0281
See application file for complete search history.

(56) References Cited

U.S. PATENT DOCUMENTS

| | | |
|---|---|---|
| 5,183,538 A | 2/1993 | Scoggins et al. |
| 2006/0137967 A1 | 6/2006 | Kister et al. |

(Continued)

FOREIGN PATENT DOCUMENTS

| | | |
|---|---|---|
| CN | 107400064 A | 11/2017 |
| CN | 107922619 A | 4/2018 |

(Continued)

OTHER PUBLICATIONS

Lee et at., Journal of Chemical Engineering of Japan, vol. 47, No. 2, pp. 87-108, 2014.*

*Primary Examiner* — Shane Fang
(74) *Attorney, Agent, or Firm* — BRYAN CAVE LEIGHTON PAISNER LLP

(57) ABSTRACT

There is provided a method and an apparatus for efficiently recovering an amide-based compound such as N-methyl-2-pyrrolidone from an aqueous solution containing an amide-based compound such as N-methyl-2-pyrrolidone.

19 Claims, 4 Drawing Sheets

(56) References Cited

U.S. PATENT DOCUMENTS

| | | | |
|---|---|---|---|
| 2009/0139852 A1 | 6/2009 | Vannuland et al. |
| 2010/0168347 A1 | 7/2010 | Butler |
| 2014/0318666 A1 | 10/2014 | Benedetti et al. |
| 2015/0051423 A1 | 2/2015 | Amoros et al. |
| 2015/0306517 A1 | 10/2015 | Lee et al. |
| 2017/0158820 A1 | 6/2017 | Miyahara et al. |
| 2018/0154278 A1 | 6/2018 | Lee et al. |
| 2018/0178141 A1 | 6/2018 | Lee et al. |
| 2018/0298145 A1 | 10/2018 | Suzuki et al. |

FOREIGN PATENT DOCUMENTS

| | | | |
|---|---|---|---|
| JP | S48-025686 A | 4/1973 |
| JP | H04-277001 A | 10/1992 |
| JP | H08-109167 A | 4/1996 |
| JP | 2002-187949 A | 7/2002 |
| JP | 2007-269638 A | 10/2007 |
| JP | 2015-078197 A | 4/2015 |
| KR | 10-2002-0095254 A | 12/2002 |
| KR | 10-2014-0030255 A | 3/2014 |
| KR | 10-2014-0092785 A | 7/2014 |
| KR | 10-2014-0092875 A | 7/2014 |
| KR | 10-2016-0118856 A | 10/2016 |
| KR | 10-2016-0144102 A | 12/2016 |
| KR | 10-1728905 B1 | 5/2017 |
| WO | 2016-047960 A1 | 3/2016 |

* cited by examiner

[FIG. 1]
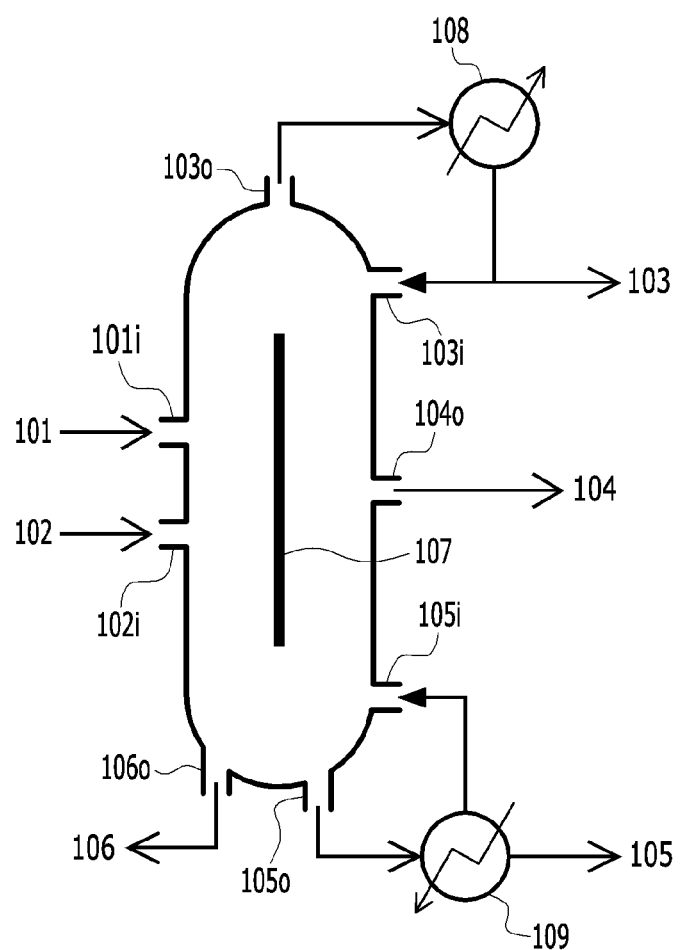

[FIG. 2]
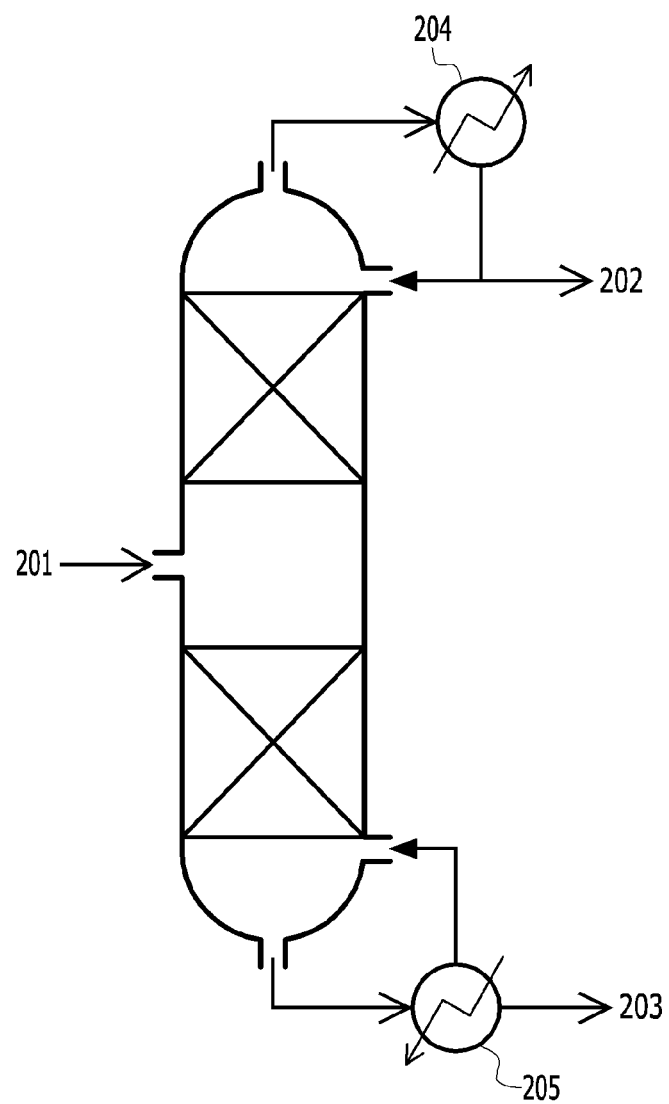

[FIG. 3]
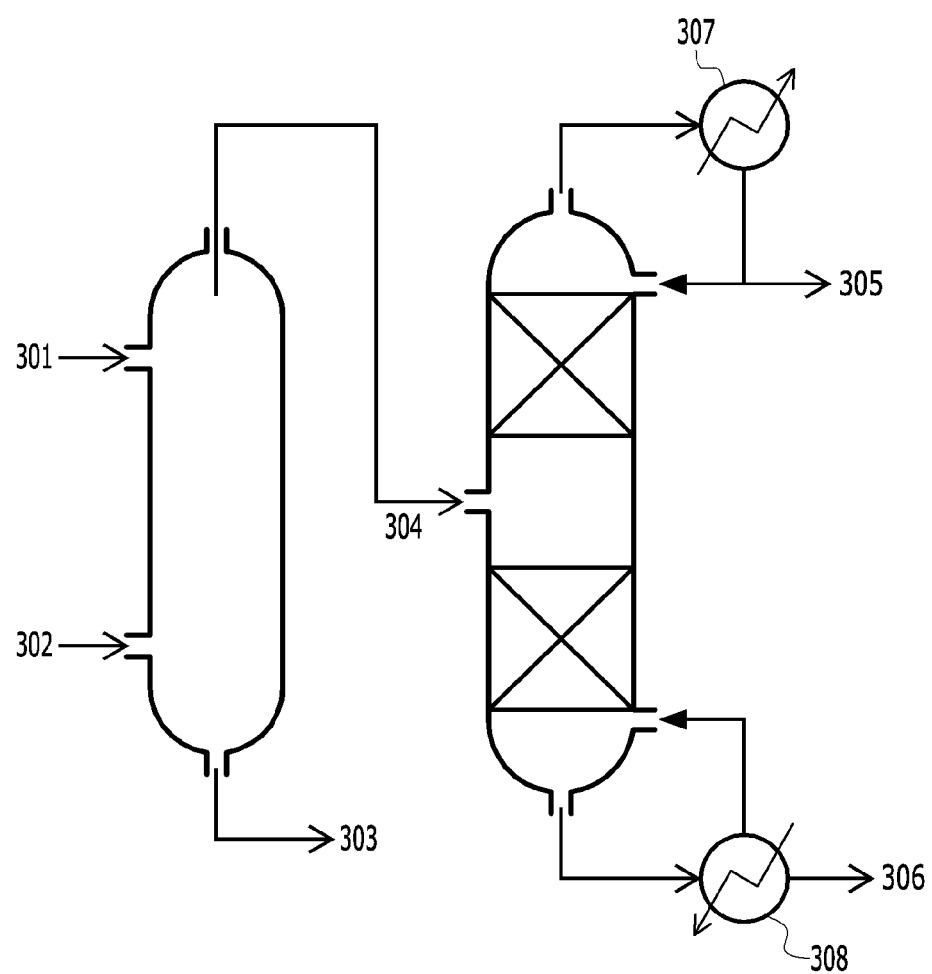

[FIG. 4]
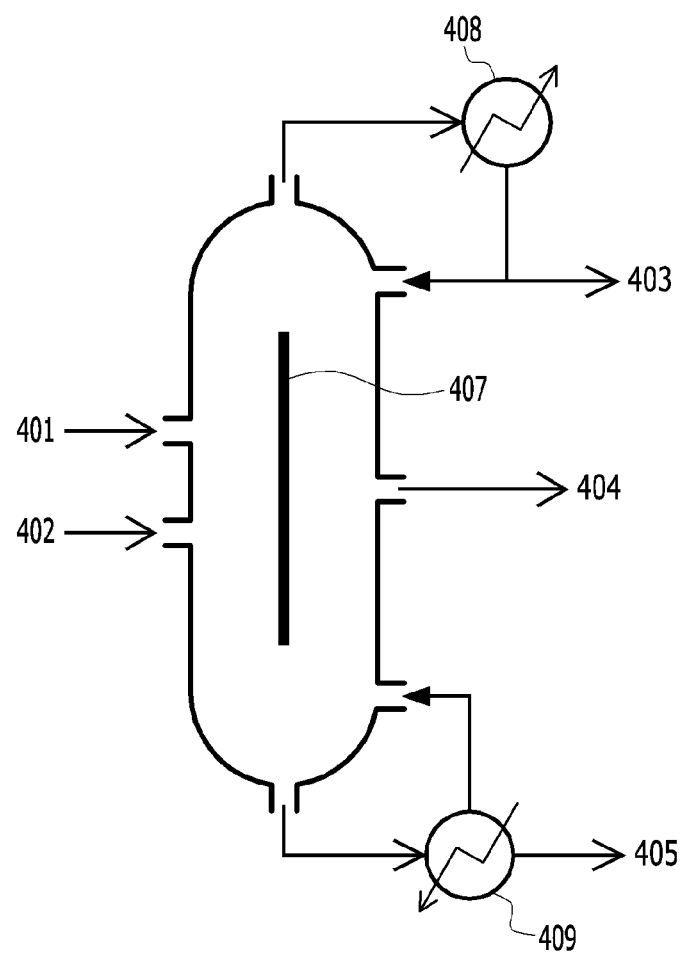

METHOD AND APPARATUS FOR RECOVERING AMIDE-BASED COMPOUND

The present application is a National Phase entry pursuant to 35 U.S.C. § 371 of International Application No. PCT/KR2019/012634 filed on Sep. 27, 2019, and claims priority to and the benefit of Korean Patent Applications No. 10-2018-0116449 filed on Sep. 28, 2018 and No. 10-2019-0119141 filed on Sep. 26, 2019 with the Korean Intellectual Property Office, the disclosures of which are incorporated herein by reference in their entirety.

FIELD

The present disclosure relates to a method and an apparatus for efficiently recovering an amide-based compound such as N-methyl-2-pyrrolidone from an aqueous solution containing an amide-based compound such as N-methyl-2-pyrrolidone.

BACKGROUND

Polyarylene sulfide (PAS), which is represented by polyphenylene sulfide (PPS), has been widely used in automobiles, electrical and electronic products, machinery and the like to replace metals, especially die cast metals such as aluminum and zinc, due to its excellent strength, heat resistance, flame retardancy, and processability. Particularly, since PPS resin has excellent flowability, it is suitable to use as a compound by kneading with a filler such as glass fiber or a reinforcing agent.

In general, a method using an amide-based compound such as N-methyl pyrrolidone (NMP) as a solvent in a PAS polymerization process is widely known in the industry. In addition, even after PAS is polymerized, remaining unreacted substance is removed by washing with an amide-based compound such as N-methyl-2-pyrrolidone (NMP) or water. The amide-based compound, such as N-methyl-2-pyrrolidone, used as described above is not only more expensive than ordinary organic solvents, but also known to be a major cause of environmental pollution when discharged in the form of an aqueous solution. Therefore, it is generally recovered, purified and reused.

However, since the amide-based compound such as N-methyl-2-pyrrolidone has high solubility in organics, it has excellent compatibility with water and it is mixed with water infinitely. In addition, when a large amount of an inorganic salt is dissolved such as an effluent from a PAS manufacturing process, it is difficult to distill as it is, so various recovery methods have been tried.

In particular, the conventional distillation process is disadvantageous in that equipment cost for increasing the number of theoretical plates of the distillation column and energy consumption are high in order to separate and recover the amide-based compound such as N-methyl-2-pyrrolidone with high purity. In addition, when an inorganic salt is dissolved such as an effluent from a PAS manufacturing process, many amide-based compounds should be left in order to ensure fluidity in the distillation column, which results in a large loss of residual components and a high treatment cost. In order to overcome these disadvantages of the distillation process, development of an extraction process or a membrane process has been attempted. However, an inorganic salt contained as an impurity in the extraction solvent was mixed and further extracted with water, and in this process, the amide-based compound was reversely extracted. Thus, due to poor separation efficiency, the technology has expired or been discarded and is not widely used.

Accordingly, there is a continuing demand for development of a process for recovering an amide-based compound capable of minimizing energy consumption of the entire process, reducing initial equipment cost, and separating compounds with high purity.

SUMMARY

The present disclosure is to provide a method and an apparatus for efficiently recovering an amide-based compound such as N-methyl-2-pyrrolidone from an aqueous solution containing an amide-based compound such as N-methyl-2-pyrrolidone.

According to one embodiment of the present disclosure, there is provided a method for recovering an amide-based compound, including the steps of: (i) introducing a mixed solution containing water and an amide-based compound, and an extraction solvent into an extraction region of a distillation column, wherein the distillation column is equipped with a dividing wall, and is divided into a column top region and a column bottom region in which the dividing wall is not located and a middle region in which the dividing wall is located, wherein the middle region is divided into the extraction region and a distillation region divided by the dividing wall, (ii) separating and discharging the amide-based compound and the extraction solvent into an upper stream of the extraction region in the distillation column, followed by separating water into a lower stream of the extraction region and discharging to a first outflow port located on the extraction region side in the column bottom region of the distillation column, and (iii) introducing at least one of the upper stream and the lower stream of the extraction region into the distillation region of the distillation column, followed by separating the extraction solvent into an upper stream of the distillation region and discharging the extraction solvent to a second outflow port of the column top region of the distillation column, separating the water into a middle stream of the distillation region and discharging the water to a third outflow port of the distillation region, and separating the amide-based compound into a lower stream of the distillation region and discharging the amide-based compound to a fourth outflow port located on the distillation region side in the column bottom region of the distillation column.

According to another embodiment of the present disclosure, there is provided an apparatus for recovering an amide-based compound that can be used in the method as described above.

According to another embodiment of the present disclosure, there is provided a preparation method of a polyarylene sulfide including the step of recovering the amide-based compound as described above.

As described above, the present disclosure may recover an amide-based compound from an aqueous solution containing an amide-based compound such as N-methyl-2-pyrrolidone by simultaneously performing an extraction process and a distillation process to improve separation efficiency, thereby minimizing energy consumption of the entire process and reducing initial equipment cost.

BRIEF DESCRIPTION OF THE DRAWINGS

FIG. 1 is a schematic illustration of a recovery apparatus and a recovery process including a dividing wall distillation column according to one embodiment of the present disclosure.

FIG. 2 is a schematic illustration of a recovery apparatus and a recovery process using a conventional distillation process according to Comparative Example 1.

FIG. 3 is a schematic illustration of a recovery apparatus and a recovery process using a conventional extraction and distillation process according to Comparative Example 2.

FIG. 4 is a schematic illustration of a recovery apparatus and a recovery process including a dividing wall distillation column performing only a distillation process without a separate liquid/liquid extraction region in a conventional manner according to Comparative Example 3.

DETAILED DESCRIPTION

In the present disclosure, the terms "the first", "the second", "the third", "the fourth", and the like are used to describe a variety of components, and these terms are merely employed to distinguish a certain component from other components.

The terminology used herein is for the purpose of describing particular embodiments only and is not intended to be limiting of the invention. The singular forms are intended to include the plural forms as well, unless the context clearly indicates otherwise. It will be further understood that the terms "include", "have", or "possess" when used in this specification, specify the presence of stated features, numbers, steps, components, or combinations thereof, but do not preclude the presence or addition of one or more other features, numbers, steps, components, or combinations thereof.

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

Hereinafter, the present invention will be described in more detail.

In the present disclosure, there are provided a method and an apparatus for efficiently recovering an amide-based compound such as N-methyl-2-pyrrolidone from an aqueous solution containing an amide-based compound such as N-methyl-2-pyrrolidone.

In particular, the present disclosure is characterized in that it is possible to minimize energy consumption of the entire process and to reduce initial equipment cost while improving separation efficiency by using an extraction process and a distillation process at the same time to efficiently separate amide-based compounds with high purity from waste liquids containing various inorganic salts and impurities generated from a polyarylene sulfide (PAS) manufacturing process.

According to one embodiment of the present disclosure, the method for recovering an amide-based compound includes the steps of: introducing a mixed solution containing water and an amide-based compound, and an extraction solvent into an extraction region of a distillation column, wherein the distillation column is equipped with a dividing wall (see 107 in FIG. 1), and is divided into a column top region and a column bottom region in which the dividing wall is not located and a middle region in which the dividing wall is located, wherein the middle region is divided into the extraction region and a distillation region divided by the dividing wall (first step, see streams 101 and 102 in FIG. 1), separating and discharging the amide-based compound and the extraction solvent into an upper stream of the extraction region in the distillation column, followed by separating water into a lower stream of the extraction region and discharging the water to a first outflow port (see stream 106 in FIG. 1) located on the extraction region side in the column bottom region of the distillation column (second step), and introducing at least one of the upper stream and the lower stream of the extraction region into the distillation region of the distillation column, followed by separating the extraction solvent into an upper stream of the distillation region and discharging the extraction solvent to a second outflow port (see stream 103 in FIG. 1) of the column top region of the distillation column, separating the water into a middle stream of the distillation region and discharging the water to a third outflow port (see stream 104 in FIG. 1) of the distillation region, and separating the amide-based compound into a lower stream of the distillation region and discharging the amide-based compound to a fourth outflow port (see stream 105 in FIG. 1) located on the distillation region side in the column bottom region of the distillation column (third step).

The method for recovering an amide-based compound is characterized in that the step of liquid/liquid extracting an aqueous solution containing an amide-based compound using an extraction solvent (second step), and the step of distilling the obtained extract (third step) are carried out simultaneously in one distillation column.

Specifically, the method for recovering an amide-based compound includes the step of introducing a mixed solution containing water and an amide-based compound, and an extraction solvent into an extraction region of the dividing wall distillation column (first step).

In particular, the method for recovering an amide-based compound may be performed using a dividing wall distillation column, as shown in FIG. 1, equipped with a dividing wall therein, and divided into a column top region and a column bottom region in which the dividing wall is not located and a middle region in which the dividing wall is located, wherein the middle region is divided into an extraction region and a distillation region divided by the dividing wall.

However, FIG. 1 is merely an example, and the scope of the method and the apparatus for recovering an amide-based compound of the present disclosure is not limited to the accompanying drawings.

The specific kind of the dividing wall distillation column which can be used in the process for recovering an amide-based compound according to the present disclosure is not particularly limited. For example, a dividing wall distillation column with a general structure as shown in FIG. 1 may be used, or a distillation column designed by changing a position or shape of the dividing wall in the distillation column to improve purification efficiency may be used. In some cases, a Petlyuk distillation column in which the extraction region and the distillation region divided by the dividing wall are included as separate columns and the column top region and the column bottom region in which the dividing wall is not located form a thermodynamically identical space by stream-connecting the extraction region and the distillation region in both directions, etc. may be used. For example, when using the Petlyuk distillation column as an alternative to the dividing wall distillation column, the Petlyuk distillation column may be in the form of a distillation column in which the region divided by the dividing wall of the dividing wall distillation column is replaced by a separate preliminary column, where top products from the preliminary column are introduced into an upper part of a subsequent column (not the dividing wall distillation column) and bottom products from the preliminary column are introduced into a lower part of the subsequent column. Herein, the preliminary column has neither a heater or a condenser nor the dividing wall, but liquid from the upper part of the subsequent column of the preliminary column and steam from the lower part of the subsequent column may be introduced into the preliminary column. In addition, the number of plates and an inner diameter of the distillation column are not particularly limited. For example, they can be set based on the number of theoretical plates derived from a distillation curve in consideration of a composition of the mixture to be purified.

Specifically, the dividing wall distillation column is an apparatus designed for distilling raw materials containing three components of low boiling point, middle boiling point and high boiling point, and is thermodynamically similar to the Petlyuk distillation column. The Petlyuk distillation column may be used as an alternative to the dividing wall distillation column. For example, the Petlyuk distillation column is designed to separate the low boiling point material and the high boiling point material in the extraction column first by adding an extraction solvent, and to separate the low boiling point material, the middle boiling point material and the high boiling point material in the distillation region by introducing the column top region of the extraction column into a feed plate of the distillation region. The dividing wall distillation column is a type in which the extraction region and the distillation region are integrated inside the column by installing a dividing wall. The present disclosure including an extraction step and a purification step using a dividing wall distillation column or a Petlyuk distillation column can recover NMP and an extraction solvent with high purity. This method is simple and very economical. By using the dividing wall distillation column or the Petlyuk distillation column, it is possible to reduce the number of distillation columns (reducing casings, heaters, condensers or internal parts of distillation column), which lowers initial investment and complexity of a distillation plant. In addition, energy consumption may be significantly reduced.

In particular, the dividing wall distillation column, unlike the Petlyuk distillation column, is inflexible to changes in operating conditions because internal circulation flow cannot be controlled once the design is determined. Thus, in the initial design stage of the distillation column, accurate simulation of various disturbances and determination of a control structure capable of easy control are necessary. In particular, depending on the nature of the compound to be distilled, the design structure such as the number of plates of the distillation column and the location of feed plate and outflow plate, and the operating conditions such as distillation temperature, pressure and reflux ratio should be changed specially. Accordingly, the present disclosure, as described above, may provide operating conditions of the dividing wall distillation column designed to separate the solvent used in the polyphenylene sulfide polymerization process with high purity and high efficiency so as to save energy and reduce equipment cost.

In one example, the dividing wall distillation column of the present disclosure may have a structure as shown in FIG. 1. As shown in FIG. 1, an exemplary dividing wall distillation column is divided by a dividing wall (107). In addition, the interior of the dividing wall distillation column may be divided into a middle region including the dividing wall, and an upper region and a lower region not including the dividing wall as shown in FIG. 1. In addition, the middle region may be divided into an extraction region and a distillation region divided by the dividing wall. For example, the dividing wall distillation column may be divided into a column top region, from which a stream of low boiling point components are discharged, a column bottom region, from which a stream of high boiling point components are discharged, an extraction region, from which a mixed solution containing water and an amide-based compound is extracted and separated with the extraction solvent, and a distillation region, from which the extraction solvent is extracted and separated into a middle stream. The term "column top region" of the dividing wall distillation column refers to a top part of the dividing wall distillation column, and may be included in the upper region of the dividing wall distillation column described above. In addition, the term "column bottom region" of the dividing wall distillation column refers to a bottom part of the dividing wall distillation column, and may be included in the lower region of the dividing wall distillation column described above. Herein, the column bottom region may be further divided into a region corresponding to the extraction region and a region corresponding to the distillation region based on a downward extension line of the dividing wall. Unless defined otherwise in the present disclosure, the upper region is used in the same sense as the column top region, and the lower region is used in the same sense as the column bottom region.

In the dividing wall distillation column of the present disclosure, the extraction region and the distillation region may be separated or isolated from each other by the dividing wall. Accordingly, it is possible to prevent a stream in the extraction region and a stream in the distillation region from mixing with each other. The term "separation or isolation" used in the present disclosure refers to a state in which a stream in each of the regions separated by the dividing wall independently flows or exists in each of the regions. In particular, the dividing wall distillation column may be configured in such a manner that the extraction region and the distillation region are included as separate columns, and the upper and lower streams of the extraction region and the distillation region are connected to each other in a separate stream. In one example, the dividing wall of the dividing wall distillation column is located in the middle region of the dividing wall distillation column. Specifically, the dividing wall of the dividing wall distillation column may be located at about 20% to about 50%, or about 25% to about 45%, of the total number of theoretical plates calculated based on the column top region. The term "the number of theoretical plates" refers to the number of hypothetical regions or plates in which two phases such as vapor and liquid phases establish equilibrium with each other in the dividing wall distillation column. When the dividing wall is located inside the dividing wall distillation column within the above range, it is possible to effectively prevent a stream in the extraction region and a stream in the distillation region from mixing with each other.

In one embodiment of the present disclosure, the dividing wall distillation column includes a feed port into which a mixed solution containing water and an amide-based compound, and an extraction solvent are introduced. The feed port of the extraction region may be composed of one port so that the mixed solution and the extraction solvent are introduced together, or may be composed of two or more ports, a first feed port into which the mixed solution containing water and an amide-based compound is introduced and a second feed port into which the extraction solvent is introduced. Through the feed port, the mixed solution containing water and an amide-based compound and the extraction solvent are introduced into the extraction region of the dividing wall distillation column.

Herein, the feed port of the extraction region may be located at 2% to 98% of the number of theoretical plates calculated based on the column top region of the distillation column. When the feed port of the extraction region is composed of two or more ports, a first feed port into which a mixed solution containing water and an amide-based compound is introduced and a second feed port into which an extraction solvent is introduced, the first feed port (see streams 101 and 101i in FIG. 1) into which the mixed solution containing water and an amide-based compound is introduced is located at 20% or less or at 2% to 20%, or at 10% or less or at 2% to 10% of the number of theoretical plates calculated based on the column top region of the distillation column, and the second feed port (see streams 102 and 102i in FIG. 1) into which the extraction solvent is introduced is located at 80% or more, or at 80% to 98%, or at 90% or more, or at 90% to 98% of the number of theoretical plates calculated based on the column top region.

In particular, the present disclosure is to efficiently separate amide-based compounds such as N-methyl-2-pyrrolidone from waste liquids containing various inorganic salts and impurities generated from a polyarylene sulfide (PAS) manufacturing process. Accordingly, the mixed solution introduced into the extraction region of the dividing wall distillation column may further contain at least one selected from the group consisting of a hydrosulfide of an alkali metal, a sulfide of an alkali metal, a halide of an alkali metal, a dihalogenated aromatic compound, and a polyarylene sulfide together with water and an amide-based compound. Specifically, the mixed solution may further contain at least one selected from the group consisting of sodium chloride (NaCl), o-dichlorobenzene (o-DCB), m-dichlorobenzene (m-DCB), p-dichlorobenzene (p-DCB), sodium hydrogen sulfide (NaSH), sodium sulfide ($Na_2S$), and polyphenylene sulfide (PPS) together with water and an amide-based compound.

For example, the waste liquid after washing generated in a polyarylene sulfide (PAS) manufacturing process may contain about 20 wt % to about 70 wt %, or about 30 wt % to about 60 wt %, of an amide-based compound such as NMP, and about 30 wt % to about 80 wt %, or about 40 wt % to about 70 wt %, of brine containing sodium chloride (NaCl). In addition, the waste liquid may further contain other impurities including p-DCB, NaSH, $Na_2S$ and dispersed PPS microparticles within about 10 wt %, or within about 5 wt %, based on a total weight of the solution medium. Other impurities include 2-pyrrolidinone, 1-methyl-2,5-pyrrolidone, 3-chloro-N-methylaniline, etc., and may include one or more of them.

Herein, specific examples of the amide-based compound may include amide compounds such as N,N-dimethylformamide or N,N-dimethylacetamide; pyrrolidone compounds such as N-methyl-2-pyrrolidone (NMP) or N-cyclohexyl-2-pyrrolidone; caprolactam compounds such as N-methyl-ε-caprolactarm; imidazolidinone compounds such as 1,3-dialkyl-2-imidazolidinone; urea compounds such as tetramethyl urea; phosphate amide compounds such as hexamethyl phosphate triamide; and the like, and the amide-based compound may include one or more of them.

In addition, the extraction solvent, which is added to the extraction region of the dividing wall distillation column with the mixed solution containing water and an amide-based compound to perform an extraction process, may be a material that is not soluble in water and has a higher boiling point than water and a lower boiling point than the amide-based compound such as NMP. Specifically, the extraction solvent may have a boiling point of about 200° C. or less or about 55° C. to about 200° C., about 180° C. or less or about 58° C. to about 180° C., or about 160° C. or less or about 60° C. to about 160° C. The extraction solvent is preferably not dissolved in water in order to effectively liquid/liquid extract the amide-based compound from an aqueous solution, and the boiling point is preferably about 200° C. or less for easy separation from the amide-based compound in the subsequent distillation process.

In addition, the extraction solvent may be at least one selected from the group consisting of an aromatic or aliphatic hydrocarbon compound having 1 to 20 carbon atoms and a compound in which at least one hydrogen of the hydrocarbon is substituted with a halogen element such as chlorine (Cl). The extraction solvent may include benzene ($C_6H_6$), chlorobenzene ($C_6H_5Cl$), chloroform ($CHCl_3$), etc., and may be one or more of them.

The extraction solvent may be added in an amount of about 100 parts by weight to 300 parts by weight, about 110 parts by weight to 280 parts by weight, or about 120 parts by weight to 250 parts by weight based on 100 parts by weight of a total weight of the mixed solution containing water and an amide-based compound.

The present disclosure uses the extraction solvent as described above in the front region of the distillation column, and the separated extract is distilled in the rear region of the same distillation column, thereby separating the amide-based compound with high purity while minimizing total energy consumption.

For example, in the first step, the mixed solution containing water and an amide-based compound and the extraction solvent may be added to the distillation column under room temperature and normal pressure conditions. Herein, the room temperature may be about 20° C. to about 30° C., and the normal pressure may mean atmospheric pressure, which is about 0.8 to 1.2 $kgf/cm^2$.

In one embodiment of the present disclosure, after the mixed solution containing water and an amide-based compound and the extraction solvent are added to the extraction region of the dividing wall distillation column, the amide-based compound and the extraction solvent are separated and discharged into an upper stream of the extraction region by the extraction process. Then, water is separated into a lower stream of the extraction region and discharged to a first outflow port (see stream 106 and outflow port 106o in FIG. 1) located on the extraction region side in the column bottom region of the distillation column (second step).

At this time, in the second step, the extraction process may be composed of about 3 to about 10 plates, preferably about 4 to about 7 plates, or about 5 to about 6 plates. The number of equilibrium plates of the extraction process is determined according to the desired degree of extraction of the solute and may be set based on the number of equilibrium plates derived from a given solvent-to-feed ratio. In addition, the extraction process may be performed at about 20° C. to 30° C. under atmospheric conditions. However, the specific process conditions related to the extraction process may be changed depending on the composition and flow rate of water and the amide-based compound, and the type and amount of the extraction solvent.

Meanwhile, the water separated into the lower stream through the liquid/liquid separation in the extraction region is separated and discharged to the first outflow port (see 106o in FIG. 1) located on the extraction region side in the column bottom region of the distillation column, and may be discharged to the outside of the distillation column or recycled to the mixed solution of the first step. Herein, a content of water in total components discharged from the first outflow port located on the extraction region side in the column bottom region of the distillation column may be about 90 wt % or more, or about 90 wt % to about 99.9 wt %, or about 95 wt % or more, or about 95 wt % to about 99.9 wt %. Herein, the residual amount other than water in the total components discharged from the first outflow port located on the extraction region side in the column bottom region of the distillation column may be an amide-based compound.

The first outflow port located on the extraction region side in the column bottom region of the distillation column is composed of one port or two or more ports, so that water may be separately discharged to the outside or recycled to the mixed solution of the first step according to the content of water in the lower stream.

In addition, the present disclosure may be configured by optimizing the number of extraction plates in the extraction region and the number of theoretical plates in the distillation region. And, the present disclosure may be configured such that the liquid/liquid separated water in the extraction region may be discharged to the outside, not to separated regions by the dividing wall such as distillation region or extraction region, as much as possible through a first outflow port (see 106o in FIG. 1) located on the extraction region side in the column bottom region of the distillation column by optimizing process conditions such as distillation temperature and reflux ratio in the distillation region. At this time, the lower stream (see 106 in FIG. 1) of the extraction region may be discharged to the outside without encountering the distillation region as pure water.

In one embodiment of the present disclosure, at least one of the upper stream and the lower stream of the extraction region is introduced into the distillation region of the distillation column, then the extraction solvent is separated into the upper stream of the distillation region and discharged to a second outflow port (see stream 103 and outflow port 103o in FIG. 1) of the column top region of the distillation column, then the water is separated into a middle stream of the distillation region and discharged to a third outflow port (see stream 104 and outflow port 104o in FIG. 1) of the distillation region, and then the amide-based compound is separated into a lower stream of the distillation region and discharged to a fourth outflow port (see stream 105 and outflow port 105o in FIG. 1) located on the distillation region side in the column bottom region of the distillation column (third step).

In the third step, the number of theoretical plates of the distillation process may be about 9 to about 25, about 12 to about 20, or about 14 to about 16. The number of theoretical plates of the distillation region may be set based on the number of theoretical plates derived from a distillation curve considering the composition of raw material.

In the distillation region, the second outflow port (see 103o in FIG. 1) discharging the distillate mainly containing the extraction solvent is located in the column top region, and the fourth outflow port (see 105o in FIG. 1) discharging the distillate mainly containing the amide-based compound is located in the column bottom region. In addition, the third outflow port (see 104o in FIG. 1) discharging the distillate mainly containing water in the middle region of the distillation column may be located at about 40% to about 65%, or about 45% to about 60%, of the number of theoretical plates calculated based on the column top region. Herein, the distillate mainly containing the extraction solvent discharged from the second outflow port (see 103o in FIG. 1) in the column top region may be separately discharged to the outside or recycled to the extraction region. At this time, a part of the stream discharged from the second outflow port may be introduced into the column top region of the dividing wall distillation column through a condenser (see 108 in FIG. 1) and an additional feed port for recycling (see 103i in FIG. 1). In addition, the distillate mainly containing water discharged from the third outflow port (see 104o in FIG. 1) of the distillation region in the middle region of the distillation column may be separately discharged to the outside or recycled to the mixed solution of the first step. In addition, the distillate mainly containing the amide-based compound discharged from the fourth outflow port (see 105o in FIG. 1) in the column bottom region may be separately discharged to the outside or recycled to the distillation region. At this time, a part of the stream discharged from the fourth outflow port may be introduced into the column bottom region of the dividing wall distillation column through a reboiler (see 109 in FIG. 1) and an additional feed port for recycling (see 105i in FIG. 1).

After the distillation process, a content of the amide-based compound in total components discharged from the second outflow port in the column top region of the distillation column may be about 10 wt % or less, or about 0.1 wt % to about 10 wt %, or about 5 wt % or less, or about 0.1 wt % to about 5 wt %. Herein, the residual amount other than the amide-based compound in the total components discharged from the second outflow port in the column top region of the distillation column may be an extraction solvent or a mixture of the extraction solvent and water. The distillate discharged from the outflow port in the column top region may be separately discharged to the outside or recycled to the extraction region or distillation region. In addition, a content of the amide-based compound in total components discharged from the fourth outflow port located on the distillation region side in the column bottom region of the distillation column may be about 90 wt % or more, or about 90 wt % to about 99.9 wt %, or about 95 wt % or more, or about 95 wt % to about 99.9 wt %. Herein, the residual amount other than the amide-based compound in total components discharged from the first outflow port located on the extraction region side in the column bottom region of the distillation column may be water.

The outflow ports located on the distillation region side in the column top region, in the column bottom region and in the middle region of the distillation column are composed of one port or two or more ports, so that the distillate may be discharged to the outside or recycled to the extraction region or distillation region according to the composition of the distillate.

In addition, the temperature and pressure conditions inside the distillation column may be controlled to a specific range in order to discharge the amide-based compound in a specific content range in the column top region and in the column bottom region as described above from the mixed solution containing water and the amide-based compound.

The temperature of the column top region of the dividing wall distillation column may be adjusted to about 50° C. to about 90° C., about 50° C. to about 80° C., or about 50° C. to about 65° C. The temperature of the column bottom region of the dividing wall distillation column may be adjusted to about 180° C. to about 220° C., about 185° C. to about 215° C., or about 190° C. to about 210° C.

At this time, the distillation process of the third step may be performed under atmospheric pressure without a separate reduced pressure or pressurized condition.

A reflux ratio of the column top stream flowing back to the column top region of the dividing wall distillation column in the column top stream of the dividing wall distillation column is about 1.0 or less, or about 0.1 to 1.0, about 0.8 or less, or about 0.15 to 0.8, or about 0.6 or less, or about 0.2 to 0.6. Herein, the "reflux ratio" means a ratio of reflux flow rate (kg/hr) with respect to outflow flow rate (kg/hr) flowing out from the distillation column.

For example, the extraction process of the second step and the distillation process of the third step are performed in one distillation column, and the same temperature, pressure, and reflux ratio are applied to the column top and bottom regions of the distillation column.

Meanwhile, according to another embodiment of the present disclosure, there is provided an apparatus for recovering an amide-based compound that can be used in the method as described above.

The apparatus for recovering an amide-based compound includes a distillation column equipped with a dividing wall; wherein the distillation column is divided into a column top region and a column bottom region in which the dividing wall is not located and a middle region in which the dividing wall is located, and the middle region is divided into an extraction region and a distillation region divided by the dividing wall; wherein the extraction region includes at least one feed port (see 101*i* and 102*i* in FIG. 1) for introducing a mixed solution containing water and an amide-based compound and an extraction solvent, and at least one first outflow port (see 106*o* in FIG. 1) for discharging liquid/liquid separated solution containing water; and an outflow port on the distillation region side consists of three streams and includes at least one second outflow port (see 103*o* in FIG. 1) for discharging separated solution of an upper stream containing an extraction solvent, at least one third outflow port (see 104*o* in FIG. 1) for discharging separated solution of a middle stream containing water, and at least one fourth outflow port (see 105*o* in FIG. 1) for discharging separated solution of a lower stream containing an amide-based compound.

Specifically, the apparatus for recovering an amide-based compound is characterized in that a mixed solution containing water and an amide-based compound and an extraction solvent are introduced into a feed port in the extraction region, and the introduced mixed solution and the extraction solvent are separated and discharged as follows: the amide-based compound and the extraction solvent are separated and discharged into an upper stream of the extraction region, and the water is separated into a lower stream of the extraction region and discharged to a first outflow port located on the extraction region side in the column bottom region of the distillation column. In addition, the apparatus for recovering an amide-based compound is characterized in that at least one of the upper stream and the lower stream of the extraction region is introduced into the distillation region of the distillation column, the extraction solvent is separated into an upper stream of the distillation region and discharged to a second outflow port of the column top region of the distillation column, the water is separated into a middle stream of the distillation region and discharged to a third outflow port of the distillation region, and the amide-based compound is separated into a lower stream of the distillation region and discharged to a fourth outflow port located on the distillation region side in the column bottom region of the distillation column.

In particular, the apparatus for recovering an amide-based compound according to the present disclosure is composed of a distillation column including an extraction region and a distillation region, thereby minimizing the number of distillation columns (casings, heaters, condensers or internal parts of distillation column) used in a purification process. Thus, the overall process efficiency can be maximized by simplifying the purification process and minimizing energy consumption. This may lower initial investment and complexity of the distillation process and significantly reduce energy consumption.

In another embodiment of the present disclosure, a configuration of the dividing wall distillation column and features related to the dividing wall, the feed port, the outflow port, the water, the amide-based compound, the extraction solvent, and the like are as described above, and a detailed description thereof will be omitted.

The apparatus for recovering an amide-based compound may further include a condenser, a reboiler, and the like. The "condenser" is a device installed separately from the distillation column, and may refer to a device for cooling the material discharged from the main column by contacting with cooling water introduced from the outside. For example, in the apparatus for recovering an amide-based compound illustrated in FIG. 1, the condenser (108) may be a device for condensing the column top stream (103) discharged from the column top region of the dividing wall distillation column. In addition, the "reboiler" is a heating device installed outside the distillation column, and it may refer to a device for reheating and evaporating a stream with a high boiling point. For example, in the apparatus for recovering an amide-based compound illustrated in FIG. 1, the reboiler (109) may be a device for heating the column bottom stream (105) discharged from the outflow port located on the distillation region side in the column bottom region of the dividing wall distillation column.

The apparatus for recovering an amide-based compound may be modified by additionally providing commonly changeable device(s) known to be usable in extraction or distillation devices.

Meanwhile, according to another embodiment of the present disclosure, there is provided a preparation method of a polyarylene sulfide including the recovery step of an amide-based compound as described above.

The preparation method of a polyarylene sulfide includes the steps of: preparing a sulfur source comprising a sulfide of an alkali metal and a mixed solvent of water and an amide-based compound by dehydrating a hydrosulfide of an alkali metal and a hydroxide of an alkali metal in a mixed solvent of water and an amide-based compound (first step of the manufacturing process); preparing a polyarylene sulfide by adding a dihalogenated aromatic compound and an amide-based compound to a reactor containing the sulfur source, and performing a polymerization reaction (second step of the manufacturing process); washing the polymerization reaction product containing the polyarylene sulfide with at least one selected from the group consisting of an amide-based compound and water (third step of the manufacturing process); introducing a mixed solution containing the water and the amide-based compound obtained in the washing step, and an extraction solvent into an extraction region of a distillation column, wherein the distillation column is equipped with a dividing wall, and is divided into a column top region and a column bottom region in which the dividing wall is not located and a middle region in which the dividing wall is located, wherein the middle region is divided into the extraction region and a distillation region divided by the dividing wall (fourth step of the manufacturing process); separating and discharging the amide-based compound and the extraction solvent into an upper stream of the extraction region in the distillation column, followed by separating water into a lower stream of the extraction region and discharging the water to a first outflow port located on the extraction region side in the column bottom region of the distillation column (fifth step of the manufacturing process), and introducing at least one of the upper stream and the lower stream of the extraction region into the distillation region of the distillation column, followed by separating the extraction solvent into an upper stream of the distillation region and discharging the extraction solvent to a second outflow port of the column top region of the distillation column, separating the water into a middle stream of the distillation region and discharging the water to a third outflow port of the distillation region, and separating the amide-based compound into a lower stream of the distillation region and discharging the amide-based compound to a fourth outflow port located on the distillation region side in the column bottom region of the distillation column (sixth step of the manufacturing process).

The preparation method of a polyarylene sulfide according to another embodiment of the present disclosure will be described in each step.

The above-described first step is preparing a sulfur source.

The sulfur source is prepared by dehydrating a hydrosulfide of an alkali metal, and a hydroxide of an alkali metal in a mixed solvent of water and an amide-based compound. Therefore, the sulfur source may include the mixed solvent of water and an amide-based compound remaining after the dehydration, together with a sulfide of an alkali metal prepared by the reaction of the hydrosulfide of an alkali metal with the hydroxide of an alkali metal.

Meanwhile, the sulfide of an alkali metal may be determined depending on the type of the hydrosulfide of an alkali metal used in the reaction. Specific examples thereof include lithium sulfide, sodium sulfide, potassium sulfide, rubidium sulfide, and cesium sulfide, and any one or a mixture of two or more thereof may be used.

Specific examples of the hydrosulfide of an alkali metal that can be used in the preparation of the sulfur source by reacting the hydrosulfide of an alkali metal with the hydroxide of an alkali metal include lithium hydrogen sulfide, sodium hydrogen sulfide, potassium hydrogen sulfide, rubidium hydrogen sulfide, cesium hydrogen sulfide, and the like. Any one or a mixture of two or more thereof may be used, and an anhydride or a hydrate thereof may be used.

Specific examples of the hydroxide of an alkali metal include lithium hydroxide, sodium hydroxide, potassium hydroxide, rubidium hydroxide, cesium hydroxide and the like, and any one or a mixture of two or more thereof may be used. The hydroxide of an alkali metal may be used in an amount of 0.90 to 2.0 equivalents, more specifically 1.0 to 1.5 equivalents, and more particularly 1.0 to 1.2 equivalents, based on 1 equivalent of the hydrosulfide of an alkali metal.

In the present disclosure, the equivalent refers to molar equivalent (eq/mol).

Further, in the preparation of the sulfur source by the reaction of the hydrosulfide of an alkali metal with the hydroxide of an alkali metal, an organic acid salt of an alkali metal capable of promoting the polymerization reaction and raising the degree of polymerization of a polyarylene sulfide in a short period of time may be added as a polymerization assistant. Specific examples of the organic acid salt of an alkali metal include lithium acetate, sodium acetate, and the like, and any one or a mixture of two or more thereof may be used. The organic acid salt of an alkali metal may be used in an amount of about 0.01 to 1.0 equivalent, specifically about 0.01 to 0.8 equivalent, and more specifically about 0.05 to 0.5 equivalent, based on 1 equivalent of the hydrosulfide of an alkali metal.

The reaction between the hydrosulfide of an alkali metal and the hydroxide of an alkali metal may be carried out in a mixed solvent of water and an amide-based compound. Specific examples of the amide-based compound include amide compounds such as N,N-dimethylformamide or N,N-dimethylacetamide; pyrrolidone compounds such as N-methyl-2-pyrrolidone (NMP) or N-cyclohexyl-2-pyrrolidone; caprolactam compounds such as N-methyl-ε-caprolactam; imidazolidinone compounds such as 1,3-dialkyl-2-imidazolidinone; urea compounds such as tetramethyl urea; phosphoric acid amide compounds such as hexamethylphosphoric acid triamide; and the like, and any one or a mixture of two or more thereof may be used. Among them, the amide-based compound may preferably be N-methyl-2-pyrrolidone (NMP), considering a reaction efficiency and a cosolvent effect as a polymerization solvent for preparing a polyarylene sulfide.

The water may be used in an amount of about 1 to 8 equivalents, specifically about 1.5 to 5 equivalents, and more specifically about 2.5 to 5 equivalents, based on 1 equivalent of the amide-based compound.

Meanwhile, in the first step, a sulfide of an alkali metal may be prepared by dehydrating reactants containing a hydrosulfide of an alkali metal, a hydroxide of an alkali metal and the like. Herein, the dehydration reaction may be performed by stirring at about 100 to 500 rpm at a temperature of about 130° C. to 205° C. More specifically, the dehydration reaction may be performed by stirring at about 100 to 300 rpm at a temperature of about 175° C. to 200° C. The dehydration reaction may be performed for about 30 minutes to 6 hours, or for about 1 hour to 3 hours.

During the dehydration reaction, the solvent such as water in the reactants may be removed by distillation or the like, and some of the amide-based compound may be discharged together with the water. In addition, some of the sulfur contained in the sulfur source may react with water by heat during the dehydration reaction, and may be volatilized as hydrogen sulfide gas.

As a result of the reaction of the hydrosulfide of an alkali metal, the hydroxide of an alkali metal and the alkali metal salt, a sulfide of an alkali metal is precipitated in a solid phase in a mixed solvent of water and an amide-based compound. Accordingly, when the sulfur source prepared by reacting the hydrosulfide of an alkali metal with the hydroxide of an alkali metal is used as a sulfur source in the preparation of a polyarylene sulfide according to the present disclosure, the molar ratio of the sulfur source refers to a molar ratio of the hydrosulfide of an alkali metal introduced during the reaction.

Subsequently, in order to remove the solvent such as water from the reaction product containing the sulfide of an alkali metal produced as a result of the above reaction, a dehydration process is performed. The dehydration process may be carried out according to a method well known in the art. The conditions are not particularly limited, and the specific process conditions are as described above.

Further, during the dehydration reaction, the sulfur contained in the sulfur source reacts with water to produce hydrogen sulfide and a hydroxide of an alkali metal, and the generated hydrogen sulfide is volatilized. Therefore, the amount of sulfur in the sulfur source remaining in the system after the dehydration reaction may be reduced by the hydrogen sulfide which is volatilized out of the system during the dehydration reaction. For example, when using the sulfur source mainly containing a hydrosulfide of an alkali metal, the amount of sulfur remaining in the system after the dehydration reaction is equal to the molar amount of sulfur in the introduced sulfur source minus the molar amount of hydrogen sulfide volatilized out of the system. Therefore, it is necessary to quantify the amount of effective sulfur contained in the sulfur source remaining in the system after the dehydration reaction from the amount of hydrogen sulfide volatilized out of the system. Specifically, the dehydration reaction is performed until the molar ratio of water to 1 mol of effective sulfur is 1 to 5, specifically 1.5 to 4, more specifically 1.75 to 3.5. When the water content in the sulfur source is excessively decreased by the dehydration reaction, water may need to be added to adjust the water content before the polymerization process.

Accordingly, the sulfur source prepared by the reaction of the hydrosulfide of an alkali metal with the hydroxide of an alkali metal and the dehydration as described above may include a mixed solvent of water and an amide-based compound together with a sulfide of an alkali metal, and the water may be included in a molar ratio of 1.75 to 3.5 based on 1 mol of sulfur contained in the sulfur source. In addition, the sulfur source may further include a hydroxide of an alkali metal prepared by the reaction of sulfur with water.

According to one embodiment of the present disclosure, the second step is polymerizing the sulfur source with a dihalogenated aromatic compound to prepare a polyarylene sulfide.

The dihalogenated aromatic compound usable for the preparation of the polyarylene sulfide is a compound in which two hydrogen atoms of an aromatic ring are substituted with halogen atoms. Specific examples thereof include o-dihalobenzene, m-dihalobenzene, p-dihalobenzene, dihalotoluene, dihalonaphthalene, dihalobiphenyl, dihalobenzoic acid, dihalodiphenyl ether, dihalodiphenylsulfone, dihalodiphenylsulfoxide, and dihalodiphenylketone, and any one or a mixture of two or more thereof may be used. In the dihalogenated aromatic compound, the halogen atom may be fluorine, chlorine, bromine or iodine. Among them, p-dichlorobenzene (p-DCB) may preferably be used in order to increase reactivity and suppress side reactions in the preparation of a polyarylene sulfide.

The dihalogenated aromatic compound may be added in an amount of about 0.8 to 1.2 equivalents based on 1 equivalent of the sulfur source. When the dihalogenated aromatic compound is added within the above range, a polyarylene sulfide having excellent physical properties may be obtained without lowering melting viscosity of the prepared polyarylene sulfide and increasing the content of chlorine present in the polyarylene sulfide. Considering the excellent effect of controlling the addition amount of the sulfur source and the dihalogenated aromatic compound, the dihalogenated aromatic compound may be added in an amount of about 0.9 to 1.1 equivalents.

Further, a step of lowering the temperature of the reactor containing the sulfur source to a temperature of about 150° C. to 200° C. may be further included before the second step to prevent vaporization of the dihalogenated aromatic compound.

Further, the polymerization reaction of the sulfur source and the dihalogenated aromatic compound may be carried out in a solvent of an amide-based compound which is a polar aprotic organic solvent and stable to an alkali at a high temperature.

Specific examples of the amide-based compound are as described above, and pyrrolidone compounds such as N-methyl-2-pyrrolidone (NMP) or N-cyclohexyl-2-pyrrolidone are preferable considering the reaction efficiency.

Since the amide-based compound contained in the sulfur source in the first step functions as a co-solvent, the amide-based compound may be added in the second step in a molar ratio of water ($H_2O$) to the amide-based compound present in the polymerization system (a ratio of water/an amide-based compound) to be about 0.85 or more.

During the polymerization reaction, other additives such as a molecular weight regulator, a cross-linking agent and the like for controlling the polymerization reaction or the molecular weight may be further added in an amount not lowering physical properties and the yield of the polyarylene sulfide to be finally prepared.

The polymerization reaction of the sulfur source and the dihalogenated aromatic compound may be performed at about 200° C. to 300° C. Alternatively, the polymerization reaction may be performed in multiple steps, varying the temperature within the above-mentioned temperature range. Specifically, after the first polymerization reaction at about 200° C. or more and less than 250° C., the second polymerization reaction may be performed at a temperature higher than that of the first polymerization reaction, specifically at about 250° C. to 300° C.

Meanwhile, the third step of the manufacturing process according to one embodiment of the present disclosure is a step of washing the polymerization reaction product using at least one selected from the group consisting of an amide-based compound and water to remove impurities, for example, oligomers or halides of alkali metal such as sodium chloride (NaCl), generated after the polymerization.

Specific examples of the amide-based compound are as described above, and the amide-based compound may preferably be N-methyl-2-pyrrolidone (NMP) in consideration of washing efficiency.

This washing process using an amide-based compound or water can be performed according to a method well known in the art, and the conditions are not particularly limited.

In addition, the mixed solution obtained by the washing process may be further subjected to a filtering step in order to remove oligomers, halides of alkali metal such as sodium chloride (NaCl), dispersed polyarylene sulfide particles (fine powder), or the like before being injected to the distillation column to be described later. This filtering process can be performed according to a method well known in the art, and the conditions are not particularly limited.

Meanwhile, the fourth to sixth steps of the manufacturing process according to one embodiment of the present disclosure relate to a process of separating and recovering the amide-based compound from the mixed solution of water and the amide-based compound obtained in the washing process, and the like.

In another embodiment of the present disclosure, features related to the process of separating and recovering the amide-based compound from the mixed solution of water and the amide-based compound are as described above, and a detailed description thereof will be omitted.

As a specific preparation method of the polyarylene sulfide and a specific method for recovering the amide-based compound, following examples may be referred to. However, the preparation method of the polyarylene sulfide or the method for recovering the amide-based compound is not limited to this description. The preparation method and the recovery method may further include a step which is usually carried out in the technical field of the present invention, and the step(s) of the preparation method may be changed by the step(s) usually changeable.

Hereinafter, the present invention will be described in more detail with reference to the following preferred examples. However, these examples are for illustrative purposes only, and the invention is not intended to be limited by these examples.

EXAMPLES

<Preparation of Polyphenylene Sulfide>
Preparation Example 1

Sodium sulfide was prepared by mixing 70% sodium hydrosulfide (NaSH) and sodium hydroxide (NaOH) in a ratio of 1:1.05 to prepare a PPS polymer. At this time, 0.33 equivalents of sodium acetate ($CH_3COONa$) powder, 1.65 equivalents of N-methyl-2-pyrrolidone (NMP), and 4.72 equivalents of deionized water (DI water) were added to the reactor. Herein, the equivalent refers to molar equivalent (eq/mol). At this time, the solid reagent was added first, followed by NMP, DI water. Then, the reactor was stirred at about 150 rpm and heated to about 215° C. to dehydrate. Thereafter, 1.04 times more equivalent of para-dichlorobenzene (p-DCB) than sodium hydrosulfide and 1.65 equivalents of N-methyl-2-pyrrolidone (NMP) were added to the reactor. Thereafter, the reaction mixture was heated to about 230° C. and reacted for about 2 hours as a front reaction, and further heated to about 255° C. and reacted for about 2 hours as a rear reaction, followed by addition of distilled water and stirring for 2 hours or more to obtain a PPS polymer as a reaction product.

After completion of the polymerization process, the reaction product was washed once with DI water and NMP at about 90° C. in order to remove residual unreacted substances or by-products, and then filtered. These washing and filtration processes were repeated twice or more times, and the final product, which is linear polyphenylene sulfide (PPS), and an aqueous medium containing NMP as a waste liquid after washing were recovered.

Herein, the waste liquid after washing contained brine (NaCl aqueous solution), which is an aqueous medium containing NMP, wherein a composition of NMP was about 20 to 70 wt % and a composition of brine containing NaCl was about 30 to 80 wt %. In addition, the waste liquid contained other impurities including fine particles such as p-DCB, NaSH, $Na_2S$, PPS fine powder, and 2-pyrrolidinone within about 10 wt % based on a total weight of the solvent of NMP and brine.

<Separation and Recovery of N-methyl-2-pyrrolidone>
Example 1

Fine powders such as NaCl and PPS were removed from the waste liquid obtained in the washing process after the PPS polymerization of Preparation Example 1 by a pretreatment process such as filtration. Then, a mixed solution containing 20 wt % of NMP and 80 wt % of water was introduced into a dividing wall distillation column equipped with a dividing wall, as shown in FIG. 1, to perform a separation and recovery process of N-methyl-2-pyrrolidone (NMP).

First, the waste liquid, which is a mixed solution containing water and NMP, and the extraction solvent were introduced into each feed port provided in an extraction region in the front part of the dividing wall distillation column, and an extraction process was performed in the extraction region. Herein, the mixed solution was introduced into the top of the extraction region located in the front part of the dividing wall (107 in FIG. 1) of the dividing wall distillation column at a flow rate of 700 kg/hr (stream 101 in FIG. 1), and chloroform ($CHCl_3$, extraction solvent) was introduced into the bottom of the extraction region at a rate of 1300 kg/hr (stream 102 in FIG. 1). A temperature of the mixed solution and the extraction solvent was 25° C. In addition, the extraction solvent was added in an amount of about 185 parts by weight based on 100 parts by weight of a total weight of the mixed solution. The mixed solution and the extraction solvent were introduced into the front part of the dividing wall distillation column to perform liquid/liquid extraction.

The extraction process in the extraction region consists of 5 plates and was operated at about 20° C. to 30° C. under atmospheric pressure. Specifically, a temperature of the column top was 24.57° C., and a temperature of the column bottom was 31.74° C. in the extraction region. As the extraction process proceeded, a mixture of low boiling point and middle boiling point, that is, water and the extraction solvent, was separated into an upper stream of the extraction region and moved to the top of the column, and a mixture of high boiling point and middle boiling point, that is, NMP and the extraction solvent was separated into a lower stream of the extraction region and moved to the bottom of the column, followed by being introduced into the distillation region in the rear part of the dividing wall distillation column. At this time, the water separated by the liquid/liquid extraction in the extraction region was discharged to the outside through an outflow port located on the extraction region side in the column bottom region (stream 106 in FIG. 1).

In the distillation region of the dividing wall distillation column, the distillation process was performed under atmospheric pressure. The distillation process was performed by introducing a mixture of the amide-based compound and the extraction solvent separated from the liquid/liquid separation in the extraction region of the front part into the distillation region of the rear part of the dividing wall distillation column having 15 theoretical plates. An operating temperature of the column top region was adjusted to be 54.36° C., and an operating temperature of the column bottom region was adjusted to be 202.12° C. in the dividing wall distillation column. A reflux ratio of the column top region of the dividing wall distillation column was 0.4, and a bottom rate was 140 kg/hr (stream 105 in FIG. 1).

As the distillation process proceeded, the extraction solvent was mainly separated into an upper stream of the distillation region, and discharged to a second outflow port of the column top region of the distillation column (stream 103 in FIG. 1), followed by being recycled to the extraction step. In addition, a middle stream of the distillation region was composed of a distillate mainly containing water (stream 104 in FIG. 1), and discharged to an outflow port of the distillation region located at 8th plate of the dividing wall distillation column, which can be recycled as raw materials. NMP was separated into a bottom stream of the distillation region, discharged to an outflow port located on the distillation region side in the column bottom region of the distillation column (stream 105 in FIG. 1), and then stored. Herein, it was confirmed that a content of NMP in the column top stream (stream 103 in FIG. 1) was within 0.1 wt % based on total components contained in the column top stream, and a content of NMP in the column bottom stream (stream 105 in FIG. 1) discharged to the bottom of the column was 99.26 wt % (pure NMP, 99% or more) based on total components contained in the column bottom stream.

In performing the separation and recovery process of N-methyl-2-pyrrolidone (NMP) according to Example 1, a composition (unit: wt %), a temperature, and a total flow rate of each stream of FIG. 1 are shown in Table 1 below.

TABLE 1

Characteristics of each stream in FIG. 1 according to Example 1

| | Stream 101 | Stream 102 | Stream 103 | Stream 104 | Stream 105 | Stream 106 |
|---|---|---|---|---|---|---|
| NMP (%) | 20 | none | less than 0.1 | 6.12 | 99.26 | less than 0.1 |
| Water (%) | 80 | none | 0.34 | less than 0.1 | less than 0.1 | 99.14 |
| Low boiling point extraction solvent (%) | none | 100 | 99.66 | 93.88 | less than 0.1 | 0.78 |
| Total flow rate (kg/hr) | 700 | 1300 | 1289 | 10 | 140 | 560 |
| Temp (° C.) | 25 | 25 | 75.3 | 117.13 | 99.26 | 18.15 |

Comparative Example 1

Fine powders such as NaCl and PPS were removed from the waste liquid obtained in the washing process after the PPS polymerization of Preparation Example 1 by a pretreatment process such as filtration. Then, a mixed solution containing 19.12 wt % of NMP and 80.88 wt % of water was introduced into a conventional distillation column, as shown in FIG. 2, to perform a separation and recovery process of N-methyl-2-pyrrolidone (NMP).

First, the mixed solution containing water and NMP (stream 201 in FIG. 2) was introduced into a mixed solution feed port located at 8th plate of the conventional distillation column having 15 theoretical plates at a flow rate of 633 kg/hr without a separate extraction solvent, followed by performing a separation process. At this time, the distillation process was performed at a column top temperature of 100.02° C. and a column bottom temperature of 173.88° C.

It was confirmed that a content of NMP in the column top stream (stream 202 in FIG. 2) was 1 wt % based on total components contained in the column top stream, and a content of NMP in the column bottom stream (stream 203 in FIG. 2) was 98 wt % based on total components contained in the column bottom stream.

In the separation and recovery process of N-methyl-2-pyrrolidone (NMP) by performing only a distillation process without a separate extraction process according to Comparative Example 1, a composition (unit: wt %), a temperature, and a total flow rate of each stream of FIG. 2 are shown in Table 2 below.

TABLE 2

Characteristics of each stream in FIG. 2 according to Comparative Example 1

| | Stream 201 | Stream 202 | Stream 203 |
|---|---|---|---|
| NMP (%) | 19.12 | less than 1 | 98 |
| Water (%) | 80.88 | 99 | less than 2 |
| Low boiling point extraction solvent (%) | none | none | none |
| Total flow rate (kg/hr) | 633 | 510 | 123 |
| Temp (° C.) | 25 | 100 | 174 |

Comparative Example 2

Fine powders such as NaCl and PPS were removed from the waste liquid obtained in the washing process after the PPS polymerization of Preparation Example 1 by a pretreatment process such as filtration. Thereafter, a mixed solution containing 20 wt % of NMP and 80 wt % of water was subjected to an extraction process by adding an extraction solvent as shown in FIG. 3, followed by a separation and recovery process of N-methyl-2-pyrrolidone (NMP) using a separate distillation apparatus.

First, the mixed solution containing water and NMP (stream 301 in FIG. 3), and chloroform (extraction solvent, stream 302 in FIG. 3) were introduced together into an extraction column, and an extraction process was performed at about 25° C. under atmospheric pressure. Herein, the extraction solvent was added in an amount of about 185 parts by weight based on 100 parts by weight of a total weight of the mixed solution. After the liquid/liquid separation was completed through this extraction process, the extract containing NMP, water, and the extraction solvent (stream 304 in FIG. 3) discharged to the upper part of the extraction column was introduced into an extract feed port located at 8th plate of the conventional distillation column having 15 theoretical plates at a flow rate of 1439 kg/hr, followed by performing a distillation process. Herein, the distillation process was performed at about 203° C. under atmospheric pressure.

Meanwhile, an effluent (stream 303 in FIG. 3) containing more than 99 wt % of water was discharged to the lower part of the column of the extraction process. NMP, the extraction solvent and water introduced into the distillation column were separated in the distillation column. Specifically, at least 99% of the extraction solvent was discharged to the upper stream of the distillation column (stream 305 in FIG. 3) and recycled to the extraction step, and pure NMP was discharged at a concentration of 99% to the lower stream of the distillation column (stream 306 in FIG. 3).

In the separation and recovery process of N-methyl-2-pyrrolidone (NMP) using a separate distillation apparatus after performing an extraction process by adding an extraction solvent according to Comparative Example 2, a composition (unit: wt %), a temperature, and a total flow rate of each stream of FIG. 3 are shown in Table 3 below.

TABLE 3

Characteristics of each stream in FIG. 3 according to Comparative Example 2

| | Stream 301 | Stream 302 | Stream 303 | Stream 304 | Stream 305 | Stream 306 |
|---|---|---|---|---|---|---|
| NMP (%) | 20 | none | less than 1 | 9.7 | less than 0.1 | 99.8 |
| Water (%) | 80 | none | 99 | 0.3 | 0.3 | less than 0.1 |
| Low boiling point extraction solvent (%) | none | 100 | less than 1 | 90 | 99.7 | 0.5 |
| Total flow rate (kg/hr) | 700 | 1300 | 561 | 1439 | 1299 | 140 |
| Temp (° C.) | 25 | 25 | 23.53 | 23.47 | 54.91 | 203.63 |

Comparative Example 3

A separation and recovery process of N-methyl-2-pyrrolidone was performed using a dividing wall distillation column equipped with a dividing wall as shown in FIG. 4 under the same conditions and in the same manner as in Example 1, except that only the distillation process was performed in both the front and rear parts of the dividing wall without an extraction region in which an liquid/liquid extraction process is performed in the front part as in the conventional method.

Specifically, the waste liquid, which is a mixed solution containing water and NMP, and the extraction solvent were introduced into each feed port (streams 401 and 402 in FIG. 4) provided in the front part of the dividing wall distillation column, and a distillation process was performed under the same conditions as in Example 1 without separate liquid/liquid extraction. Water and the extraction solvent were discharged to an upper stream of the column top region (stream 403 in FIG. 4), the distillate mainly containing the extraction solvent was discharged to a middle stream (stream 404 in FIG. 4), and NMP and some water were discharged to a bottom stream of the column bottom region (stream 405 in FIG. 4). Herein, it was confirmed that a content of NMP in the column top stream (stream 403 in FIG. 4) was within 1 wt % based on total components contained in the column top stream, which is similar to Example 1. However, a content of NMP in the column bottom stream (stream 405 in FIG. 4) discharged to the bottom of the column was only 82.1 wt % based on total components contained in the column bottom stream.

In performing the separation and recovery process of N-methyl-2-pyrrolidone (NMP) according to comparative Example 3, a composition (unit: wt %), a temperature, and a total flow rate of each stream of FIG. 4 are shown in Table 4 below.

TABLE 4

Characteristics of each stream in FIG. 4 according to Comparative Example 3

| | Stream 401 | Stream 402 | Stream 403 | Stream 404 | Stream 405 |
|---|---|---|---|---|---|
| NMP (%) | 20 | none | less than 0.1 | 1.1 | 82.10 |
| Water (%) | 80 | none | 77.28 | 1.4 | 17.89 |
| Low boiling point extraction solvent (%) | none | 100 | 22.71 | 97.5 | less than 0.1 |
| Total flow rate (kg/hr) | 700 | 1550 | 1570 | 540 | 140 |
| Temp (°C) | 25 | 25 | 75.3 | 110.41 | 144.90 |

<Experimental Example 1>

In the separation and recovery process of N-methyl-2-pyrrolidone (NMP) according to Example 1 and Comparative Examples 1 to 2, energy consumption and purity of the final product were evaluated by the following method, and the results are shown in Table 5 below.

1) Total Energy Consumption ($\times 10^6$ kJ/hr)

The total energy consumption used in the recovery process of Examples and Comparative Examples was measured over time for equivalent raw material input and purity of the final recovered product.

2) Purity of Final Recovered Product (%)

The purity (%) of NMP and water in the final recovered product was measured for equivalent raw material input.

TABLE 5

| | | Comp. Ex. 1 | Comp. Ex. 2 | Example 1 |
|---|---|---|---|---|
| Total energy consumption ($\times 10^6$ KJ/hr) | | 1.03 | 3.78 | 0.9 |
| Purity of recovered product | NMP (%) | 99 | 98 | 99 |
| | Water (%) | 99 | 99 | 99 |

As shown in Table 5, it was confirmed that the total energy consumption used in the recovery process of Example 1 according to the present disclosure was significantly reduced compared to the total energy consumption used in the recovery process using the distillation apparatus of Comparative Example 1 to 2.

Specifically, when separating NMP and water using the dividing wall distillation column according to Example 1 of the present disclosure, the total energy consumption was reduced by about $0.13 \times 10^6$ kJ/hr, which is about 12.6%, compared to the recovery process using a distillation column in the conventional manner according to Comparative Example 1. In addition, the recovery process according to Example 1 reduced the total energy consumption by about $2.88 \times 10^6$ kJ/hr, which is about 76.2%, compared to the recovery process in which the extraction and distillation processes were operated separately according to Comparative Example 2.

Example 2

A separation and recovery process of N-methyl-2-pyrrolidone (NMP) was performed under the same conditions and in the same manner as in Example 1, except that a waste liquid containing 140 kg/hr of NMP and 560 kg/hr of water was injected at 45° C., 3.5 atm in a feed stream to a dividing wall distillation column, and 4800 kg/hr of chlorobenzene ($C_6H_5Cl$) was injected at 55° C., 3.5 atm in an extraction solvent stream under the conditions as shown in Table 6 below. Herein, the dividing wall distillation column has five plates of extraction region and 15 plates of distillation region, and a reflux ratio was 0.2 and a bottoms rate was 135 kg/hr.

As a result of performing the separation and recovery process of N-methyl-2-pyrrolidone (NMP) according to Example 2, 552.6 kg/hr of water (purity: 99.8 mol %) was recovered through an outflow port located on the extraction region side in the column bottom region (stream 106 in FIG. 1). Herein, a recovery rate of water (%) was 98.7%, obtained by dividing the 'amount of water recovered (kg)' by the 'amount of water injected in the feed stream (kg)'. In addition, a content of NMP in the column top stream (stream 103 in FIG. 1) was within 0.1 wt % based on total components contained in the column top stream, and 134.4 kg/hr of NMP (purity: 99.6 mol %) was recovered through a column bottom stream discharged to the lower part of the column (stream 105 in FIG. 1). Herein, a recovery rate of NMP (%) was 96%, and the recovery rate of water (%) was obtained by dividing the 'amount of water recovered (kg)' by the 'amount of water injected in the feed stream (kg)'.

The energy consumption used in the separation and recovery process of N-methyl-2-pyrrolidone (NMP) according to Example 2 was 1338.3 kW.

Example 3

A separation and recovery process of N-methyl-2-pyrrolidone (NMP) was performed in the same manner as in Example 2, except that a waste liquid containing 280 kg/hr of NMP and 420 kg/hr of water was injected in a feed stream, and temperatures of the column top and the column bottom were changed as shown in Table 6 below. Herein, a bottoms rate was 277 kg/hr.

As a result of performing the separation and recovery process of N-methyl-2-pyrrolidone (NMP) according to Example 3, 406.74 kg/hr of water (purity: 99.8 mol %) was recovered through an outflow port located on the extraction region side in the column bottom region (stream 106 in FIG. 1). Herein, a recovery rate of water (%) was 96.8%. In addition, a content of NMP in the column top stream (stream 103 in FIG. 1) was within 0.1 wt % based on total components contained in the column top stream, and 275.8 kg/hr of NMP (purity: 99.6 mol %) was recovered through a column bottom stream discharged to the lower part of the column (stream 105 in FIG. 1). Herein, a recovery rate of NMP (%) was 98.5%.

The energy consumption used in the separation and recovery process of N-methyl-2-pyrrolidone (NMP) according to Example 3 was 1392.9 kW.

Example 4

A separation and recovery process of N-methyl-2-pyrrolidone (NMP) was performed in the same manner as in Example 2, except that a waste liquid containing 560 kg/hr of NMP and 140 kg/hr of water was injected in a feed stream, and temperatures of the column top and the column bottom were changed as shown in Table 6 below. Herein, a bottoms rate was 555 kg/hr.

As a result of performing the separation and recovery process of N-methyl-2-pyrrolidone (NMP) according to Example 4, 105.6 kg/hr of water (purity: 99.8 mol %) was recovered through an outflow port located on the extraction region side in the column bottom region (stream 106 in FIG. 1). Herein, a recovery rate of water (%) was 96.8%. In addition, a content of NMP in the column top stream (stream 103 in FIG. 1) was within 0.1 wt % based on total components contained in the column top stream, and 554.9 kg/hr of NMP (purity: 99.9 mol %) was recovered through a column bottom stream discharged to the lower part of the column (stream 105 in FIG. 1). Herein, a recovery rate of NMP (%) was 98.5%.

The energy consumption used in the separation and recovery process of N-methyl-2-pyrrolidone (NMP) according to Example 4 was 712.1 kW.

Comparative Example 4

A separation and recovery process of N-methyl-2-pyrrolidone (NMP) was performed in the same manner as in Comparative Example 3 by performing only a distillation process without a liquid/liquid extraction process using a dividing wall distillation column, except that a waste liquid containing 140 kg/hr of NMP and 560 kg/hr of water was injected at 45° C., 3.5 atm in a feed stream to a dividing wall distillation column, and 4800 kg/hr of chlorobenzene ($C_6H_5Cl$) was injected at 55° C., 3.5 atm in an extraction solvent stream under the conditions as shown in Table 6 below. Herein, the dividing wall distillation column has only 20 plates of distillation region (i.e., 5 plates of prefractionator and 15 plates of distillation region) without separate extraction region, and a reflux ratio was 0.2 and a bottoms rate was 135 kg/hr.

As a result of performing the separation and recovery process of N-methyl-2-pyrrolidone (NMP) according to Comparative Example 4, 552.6 kg/hr of water (purity: 98.6 mol %) was recovered (stream 403 in FIG. 4). Herein, a recovery rate of water (%) was 98.7%. In addition, 131 kg/hr of NMP (purity: 94.2 mol %) was recovered through a column bottom stream discharged to the lower part of the column (stream 405 in FIG. 4). Herein, a recovery rate of NMP (%) was 94.2%.

The energy consumption used in the separation and recovery process of N-methyl-2-pyrrolidone (NMP) according to Comparative Example 4 was 1802.5 kW.

<Experimental Example 2>

The main conditions of the separation and recovery process of N-methyl-2-pyrrolidone (NMP) according to Examples 2 to 4 and Comparative Example 4 are summarized below. Purity and a recovery rate of the recovered water and NMP, and energy consumption used in the separation and recovery process of N-methyl-2-pyrrolidone (NMP) were measured and evaluated in the same manner as in Experimental Example 1 described above, and the results are shown in Table 6 below.

TABLE 6

|  | Ex. 2 | Ex. 3 | Ex. 4 | Comp. Ex. 4 |
|---|---|---|---|---|
| Flow rate of mixed solution (including water and NMP) (kg/hr) | 700 | 700 | 700 | 700 |
| Composition of mixed solution (water: NMP) | 80:20 | 60:40 | 40:60 | 80:20 |
| Number of plates (extraction region/ distillation region) | 5/15 | 5/15 | 5/15 | 0/20 (5/15) |
| Top temp. of distillation region (° C.) | 80.8 | 69.0 | 53.7 | 74.4 |
| Bottom temp. of distillation region (° C.) | 202.8 | 202.8 | 203.4 | 195.0 |
| Reflux ratio of distillation region | 0.2 | 0.2 | 0.2 | 0.2 |
| Purity of NMP (mol %) | 99.6 | 99.6 | 99.6 | 94.2 |
| Recovery rate of NMP (%) | 96 | 98.5 | 98.5 | 93.6 |
| Purity of water (mol %) | 99.8 | 99.8 | 99.8 | 98.6 |
| Recovery rate of water (%) | 98.7 | 96.8 | 96.8 | 98.7 |
| Energy consumption (KW) | 1338.3 | 1392.9 | 712.1 | 1802.5 |

As shown in Table 6 above, as Examples 2 to 4 according to the present disclosure discharged the water separated through the extraction region to the lower stream, the water was not back-mixed compared to comparative Example 4 and the purity of the recovered amide-based compound, water, extraction solvent, and the like were high, resulting in excellent separation efficiency. In particular, in the case of Examples 2 to 4, not only the purity and recovery rate of the recovered water and NMP were higher than those of Comparative Example 4, which performed the distillation process with the same reflux ratio, but also the energy consumption was significantly reduced.

DESCRIPTION OF SYMBOLS

101: Mixed solution feed stream of dividing wall distillation column

101*i*: First feed port for introducing mixed solution of dividing wall distillation column

102: Extraction solvent feed stream of dividing wall distillation column

102*i*: Second feed port for introducing extraction solvent of dividing wall distillation column

103: Column top stream of dividing wall distillation column

103*i*: Additional feed port for recirculating column top stream of dividing wall distillation column

103*o*: Second outflow port for discharging column top vapor outflow stream of dividing wall distillation column

104: Side stream of dividing wall distillation column

104*o*: Third outflow port for discharging side stream of dividing wall distillation column

105: Column bottom stream of dividing wall distillation column

105*o*: Fourth outflow port for discharging column bottom stream of dividing wall distillation column

105*i*: Additional feed port for recirculating column bottom stream of dividing wall distillation column

106: Liquid/liquid separation outflow stream of dividing wall distillation column 106o: First outflow port for discharging liquid/liquid separation stream of dividing wall distillation column
107: Dividing wall of dividing wall distillation column
201: Mixed solution feed stream of distillation column
202: Column top stream of distillation column
203: Column bottom stream of distillation column
301: Mixed solution feed stream of extraction column
302: Extraction solvent feed stream of extraction column
303: Column bottom stream of extraction column
304: Extract feed stream of distillation column
305: Column top stream of distillation column
306: Column bottom stream of distillation column
401: Mixed solution feed stream of dividing wall distillation column
402: Extraction solvent feed stream of dividing wall distillation column
403: Column top stream of dividing wall distillation column
404: Side stream of dividing wall distillation column
405: Column bottom stream of dividing wall distillation column
407: Dividing wall of dividing wall distillation column
108, 204, 307, 408: Condenser of distillation column
109, 205, 308, 409: Reboiler of distillation column

The invention claimed is:

1. A method for recovering an amide-based compound, comprising the steps of:
   (i) introducing a mixed solution containing water and an amide-based compound, and an extraction solvent, into an extraction region of a distillation column, wherein the extraction region comprises at least one feed port for introducing the mixed solution containing water and the amide-based compound and the extraction solvent, and wherein the feed port of the extraction region is located at 2% to 98% of the number of theoretical plates calculated based on the column top region of the distillation column, wherein the distillation column is equipped with a dividing wall, and is divided into a column top region and a column bottom region in which the dividing wall is not located and a middle region in which the dividing wall is located, wherein the middle region is divided into the extraction region and a distillation region divided by the dividing wall,
   (ii) separating and discharging the amide-based compound and the extraction solvent into an upper stream of the extraction region in the distillation column, followed by separating water into a lower stream of the extraction region and discharging the water to a first outflow port located on the extraction region side in the column bottom region of the distillation column, and
   (iii) introducing at least one of the upper stream and the lower stream of the extraction region into the distillation region of the distillation column, followed by separating the extraction solvent into an upper stream of the distillation region and discharging the extraction solvent to a second outflow port of the column top region of the distillation column, separating the water into a middle stream of the distillation region and discharging the water to a third outflow port of the distillation region, and separating the amide-based compound into a lower stream of the distillation region and discharging the amide-based compound to a fourth outflow port located on the distillation region side in the column bottom region of the distillation column.

2. The method for recovering an amide-based compound according to claim 1, wherein the upper stream of the extraction region and the upper stream of the distillation region coexist in the column top region of the distillation column, and the lower stream of the extraction region and the lower stream of the distillation region coexist in the column bottom region of the distillation column.

3. The method for recovering an amide-based compound according to claim 1, wherein a content of water in total components discharged from the first outflow port located on the extraction region side in the column bottom region of the distillation column is 90 wt % or more, a content of the amide-based compound in total components discharged from the second outflow port in the column top region of the distillation column is 10 wt % or less, and a content of the amide-based compound in total components discharged from the fourth outflow port located on the distillation region side in the column bottom region of the distillation column is 90 wt % or more.

4. The method for recovering an amide-based compound according to claim 1, wherein the extraction solvent has a boiling point of 200° C. or less.

5. The method for recovering an amide-based compound according to claim 1, wherein the extraction solvent is at least one selected from the group consisting of benzene, chlorobenzene, and chloroform.

6. The method for recovering an amide-based compound according to claim 1, wherein the mixed solution is a waste liquid generated in a synthesizing and washing process of a polyarylene sulfide.

7. The method for recovering an amide-based compound according to claim 1, wherein in step (i), the extraction solvent is added in an amount of 100 parts by weight to 300 parts by weight based on 100 parts by weight of a total weight of the mixed solution containing water and an amide-based compound.

8. The method for recovering an amide-based compound according to claim 1, wherein in step (ii), the extraction process is performed at 20° C. to 35° C.

9. The method for recovering an amide-based compound according to claim 1, wherein in step (ii), the extraction process is performed such that the number of extraction plates is 3 to 10.

10. The method for recovering an amide-based compound according to claim 1, wherein a temperature of the column top region in the distillation column is adjusted to 50° C. to 90° C.

11. The method for recovering an amide-based compound according to claim 1, wherein a temperature of the column bottom region in the distillation column is adjusted to 180° C. to 220° C.

12. The method for recovering an amide-based compound according to claim 1, wherein the distillation process is performed such that the number of theoretical plates of the distillation column is 9 to 25.

13. The method for recovering an amide-based compound according to claim 1, wherein a reflux ratio of the column top region in the distillation column is adjusted to 1.0 or less.

14. An apparatus for recovering an amide-based compound, comprising a distillation column equipped with a dividing wall,
   wherein the distillation column is divided into a column top region and a column bottom region in which the dividing wall is not located, and a middle region in which the dividing wall is located, and the middle region is divided into an extraction region and a distillation region divided by the dividing wall,
   wherein the extraction region comprises at least one feed port for introducing a mixed solution containing water and an amide-based compound and an extraction solvent, wherein the feed port of the extraction region is located at 2% to 98% of the number of theoretical plates calculated based on the column top region of the distillation column, and at least one first outflow port for discharging liquid/liquid separated solution containing water, and an outflow port on the distillation region side and comprises at least one second outflow port for discharging separated solution of an upper stream containing an extraction solvent, at least one third outflow port for discharging separated solution of a middle stream containing water, and at least one fourth outflow port for discharging separated solution of a lower stream containing an amide-based compound.

15. The apparatus for recovering an amide-based compound according to claim 14, wherein the dividing wall of the distillation column is located at 20% to 50% of the number of theoretical plates calculated based on the column top region.

16. The apparatus for recovering an amide-based compound according to claim 14, wherein the feed port of the extraction region in the distillation column comprises two or more ports; a first feed port into which a mixed solution containing water and an amide-based compound is introduced and a second feed port into which an extraction solvent is introduced.

17. The apparatus for recovering an amide-based compound according to claim 16, wherein the first feed port is located at 20% or less of the number of theoretical plates calculated based on the column top region of the distillation column, and the second feed port is located at 90% or more of the number of theoretical plates calculated based on the column top region of the distillation column.

18. The apparatus for recovering an amide-based compound according to claim 14, wherein in the distillation column, the first outflow port on the extraction region side is fixed in a column bottom region on the lower region of the column, the second outflow port and the fourth outflow port on the distillation region side are fixed in a column top region on the upper region of the column and in a column bottom region on the lower region of the column, respectively, and the third outflow port is located at 40% to 65% of the number of theoretical plates calculated based on the column top region of the distillation column.

19. A preparation method of a polyarylene sulfide, comprising the steps of:

preparing a sulfur source comprising a sulfide of an alkali metal and a mixed solvent of water and an amide-based compound by dehydrating a hydrosulfide of an alkali metal and a hydroxide of an alkali metal in a mixed solvent of water and an amide-based compound;

preparing a polyarylene sulfide by adding a dihalogenated aromatic compound and an amide-based compound to a reactor containing the sulfur source, and performing a polymerization reaction;

washing the polymerization reaction product containing the polyarylene sulfide with at least one selected from the group consisting of an amide-based compound and water; introducing a mixed solution obtained in the washing step, and an extraction solvent, into an extraction region of a distillation column, wherein the extraction region comprises at least one feed port for introducing the mixed solution, wherein the feed port of the extraction region is located at 2% to 98% of the number of theoretical plates calculated based on the column top region of the distillation column, wherein the mixed solution contains water and an amide-based compound, and wherein the distillation column is equipped with a dividing wall, and is divided into a column top region and a column bottom region in which the dividing wall is not located and a middle region in which the dividing wall is located, wherein the middle region is divided into the extraction region and a distillation region divided by the dividing wall, separating and discharging the amide-based compound and the extraction solvent into an upper stream of the extraction region in the distillation column, followed by separating water into a lower stream of the extraction region and discharging the water to a first outflow port located on the extraction region side in the column bottom region of the distillation column, and introducing at least one of the upper stream and the lower stream of the extraction region into the distillation region of the distillation column, followed by separating the extraction solvent into an upper stream of the distillation region and discharging the extraction solvent to a second outflow port of the column top region of the distillation column, separating the water into a middle stream of the distillation region and discharging the water to a third outflow port of the distillation region, and separating the amide-based compound into a lower stream of the distillation region and discharging the amide-based compound to a fourth outflow port located on the distillation region side in the column bottom region of the distillation column.

* * * * *